United States Patent [19]

Koehler et al.

[11] Patent Number: 5,559,270
[45] Date of Patent: Sep. 24, 1996

[54] METHOD OF SYNTHESIZING PURE ADDITIVES AND THE IMPROVED COMPOSITIONS THEREBY PRODUCED

[75] Inventors: Donald E. Koehler, Mentor; William J. Claffey, Novelty, both of Ohio

[73] Assignee: Petrokleen, Ltd., Cleveland, Ohio

[21] Appl. No.: 356,700

[22] Filed: Dec. 15, 1994

[51] Int. Cl.⁶ .................................................. C07C 209/06
[52] U.S. Cl. ....................... 564/484; 564/470; 564/474; 564/481; 564/509; 564/511; 564/512
[58] Field of Search ................................. 564/470, 509, 564/511, 512, 484, 481

[56] References Cited

U.S. PATENT DOCUMENTS

| | | | |
|---|---|---|---|
| 3,753,670 | 8/1973 | Strang et al. | 44/432 |
| 3,756,793 | 9/1973 | Robinson | 44/432 |
| 3,785,790 | 1/1974 | Strang | 44/372 |
| 3,864,098 | 2/1975 | Honnen | 44/334 |
| 3,876,704 | 4/1975 | Nakaguchi | 564/503 |
| 3,951,614 | 4/1976 | Honnen | 44/331 |
| 4,357,148 | 11/1982 | Graiff | 44/432 |
| 5,006,130 | 4/1991 | Aiello | 44/432 |

FOREIGN PATENT DOCUMENTS

| | | |
|---|---|---|
| 1083610 | 9/1967 | United Kingdom . |
| 1419957 | 12/1973 | United Kingdom . |

*Primary Examiner*—Brian Burn
*Attorney, Agent, or Firm*—Fay, Sharpe, Beall, Fagan, Minnich & McKee

[57] ABSTRACT

An improved process of synthesizing gasoline soluble polyolefinic amines or polyether amines comprising the steps of reacting polyolefinic halides or polyether halides with polyamines in a specific sequence of reactions; distilling off non-reactive polyamine; neutralizing the reaction mixture; recovering polyamine(s) and water; and separating polyolefinic amines from the solids with simple filtration or centrifuge or decanting.

13 Claims, No Drawings

METHOD OF SYNTHESIZING PURE ADDITIVES AND THE IMPROVED COMPOSITIONS THEREBY PRODUCED

BACKGROUND OF THE INVENTION

The present invention relates to an improved method of synthesizing polyamines containing at least one olefinic polymer chain or oil soluble polyether. It concerns the improved fuel additives thereby produced, and the resultant improved fuel composition which comprises an admixture of said fuel additive and a gasoline.

It is known that oil soluble polyamines containing at least one olefinic polymer chain or oil soluble polyether can be employed to improve the detergent properties of fuel and lubricant compositions. The use of such compositions, their utility in providing a fuel with significantly reduced octane requirement increase (ORI) characteristics; removal and/or beneficial modification of deposits in the combustion chamber, intake valves and the like; as well as potential improvement in fuel efficiency are taught by a number of prior patents including U.S. Pat. Nos. 3,275,554; 4,438,757; 3,565,804; 3,574,576; 3,898,056; 3,960,515; 4,022,589; and, 4,039,300, the disclosures and claims of all of which are specifically incorporated herein by reference. Such polyamines have been used both alone and in combination with other additives, particularly polymeric additives.

The polyamines described in this invention contains at least one olefinic polymer derived from alkanes or alkenes with straight or branched chains, which may or may not have aromatic or cycloaliphatic substituents, for instance, groups derived from polymers or copolymers of olefins which may or may not have a double bond. Examples of non-substituted alkenyl and alkyl groups are polyethylene groups, polypropylene groups, polybutylene groups, polyisobutylene groups, polyethylene-polypropylene groups, polyethylene-poly-alpha-methyl styrene groups and the corresponding groups without double bonds. Particularly preferred are polypropylene and especially polyisobutylene groups, or oil soluble polyethers such as copolymers of ethylene oxide and propylene oxide.

The polyamines used to form the polyamine compounds of this invention include primary, secondary, and tertiary low molecular weight aliphatic polyamines such as ethylene diamine, diethylenetriamine, triethylenetetramine, dimethylaminopropylamine, propylene diamine, butylene diamine, trimethyl trimethylene diamine, tetramethylene diamine, diaminopentane or pentamethylene diamine, hexamethylene diamine, heptamethylene diamine, diaminooctane, decamethylene diamine, and higher homologues up to about 18 carbon atoms. In the preparation of these compounds, the same amines can be used or substituted amines can be used such as N-methyl ethylene diamine, N-propyl ethylene diamine, N,N-dimethyl 1,3-propane diamine, N-2- hydroxypropyl ethylene diamine, penta-(1-methylpropylene) hexamine, tetrabutylene-pentamine, hexa-(1,1-dimethylethylene) heptane, di-(1-methylamylene)-triamine, tetra-(1,3-dimethylpropylene)pentamine, penta-(1,5-dimethylamylene) hexamine, di(1-methyl-4-ethylbutylene)triamine, penta-(1,2-dimethyl-1-isopropyl ethylene)hexamine, tetraoctylenepentamine and the like.

Compounds possessing triamine as well as tetramine and pentamine groups are applicable for use because these can be prepared from technical mixtures of polyethylene polyamines, which could offer economic advantages.

The polyamine can be a cyclic polyamine, for instance, the cyclic polyamines formed when aliphatic polyamines with nitrogen atoms separated by ethylene groups were heated in the presence of hydrogen chloride.

The polymeric components are well known in the art and numerous patents exists which relate to their manufacture, such as U.S. Pat. No. 3,275,554.

The efficacy of the additive is a function of the nitrogen content, and/or the presence of a terminal primary amine moiety. However, terminal primary amine additives prepared according to prior art contain significant and often undesirable quantities of dimer and trimer. When terminal amine is a tertiary amine, or a sterically hindered secondary amine, there is no dimerization and the efficacy of such additives is greater than those containing dimers but inferior to additives containing only primary terminal amines.

The dimers significantly reduce the nitrogen concentration and reduce or eliminate the benefits of the nitrogen increased molecular-weight, they also result in increased overall molecular weight and higher viscosity requiring a higher concentration of additive in order to achieve the same overall effect.

Until now, those additives that are manufactured to maximize monomer concentration have generally been produced by reacting a polyolefinic halide with a substantial stoichiometric excess of amine to reduce, though not totally eliminate, the formation of dimers and trimers. The use of such a stoichiometric excess of amine, however, results in a substantial negative impact to the manufacturing costs because of the significant quantity of excess amine that must be continuously purified and recycled, and the reduction in effective reactor volume.

SUMMARY OF THE INVENTION

The present invention provides a method of synthesizing polyolefinic amines, having a reduced concentration of dimers and/or trimers. It comprises the steps of:

(a) forming a polyolefinic halide or polyether halide;

(b) reacting the polyolefinic halide or polyether halide with less than one molar equivalent (i.e. from about 0.99 to about 0.01 molar equivalent) of a polyamine having only one reactive amine, for a period of from about 0.5 to about 15.0 hours at a temperature of from about 75° F. to about 410° F. and a pressure of from about 0 to about 6 atmospheres;

(c) adding to the reaction mass at least one additional polyamine having at least two reactive amine moieties, in an amount equal to from 1 to about 10 times the molar quantity of polyolefinic halide or polyether halide employed to form the first reaction mass and reacting the second reaction mass for a period of from about 0.5 to about 15 hours at a temperature of from about 75° F. to about 410° F. and a pressure of from about 0 to about 6 atmospheres;

(d) distilling off any unreacted polyamine at a distillation temperature below about 400° F.; and, (e) treating the second reaction mass to recover polyolefinic or polyether amine products.

The present invention also encompasses the fuel additive product produced by the foregoing process, and the novel motor fuel composition containing an amount of this additive of 0.5–5.0 ppm, expressed as basic nitrogen. This will inhibit octane requirement increase (ORI) and clean up the induction system. For simplification, except as otherwise clear from the context, the term "polymeric halide" shall be understood to include both polyolefin halides, polyether halides, and/or mixtures of such halides and "polyolefinic amines" shall be understood to include both polyolefinic amines and polyether amines.

Still further, the present invention encompasses a method of producing polyolefinic amine or polyether amine which facilitates separation of amine hydrochloride from polyolefinic amine or polyether amine product without the use of a plurality of aqueous washing steps. This is possible because of improved amine hydrochloride crystal size and morphology which facilitate the separation of any amine hydrochloride salts from the polyolefinic amine or polyether amine.

THE PREFERRED EMBODIMENT

In the preferred process of the present invention, the preferred polymer is a polyolefinic halide, such as polyisobutylenechloride, the first polyamine, having only a single reactive amine, is a polyamine in which all other amine moieties are hindered, such as for example DMAPA, and the second polyamine is one having at least two or more primary amine moieties such as for example EDA or tetraethylenepentamine.

There are, of course, any number of equally suitable materials which may be utilized in the practice of the present invention; however, the remaining discussion will center primarily on the use of polyisobutylene, EDA, and DMAPA, because these reactants are readily commercially available. Again, the various United States patents previously incorporated herein by reference all list a number of suitable amines for use in the synthesis of additives such as those contemplated by the present invention.

As specific illustrations of the preparation of products by the process in the present invention, the following examples are presented by way of illustration and not by way of limitation.

PREPARATION OF POLYMERIC HALIDES

In a flask, 1000 grams of the desired polyolefin having an average molecular weight of 950 was contacted with about 97 grams of chlorine gas. The temperature was maintained between 95° and 105° C. for about 4 hours. A 30 minute nitrogen purge was used to remove suspended chlorine and HCl from the polyolefinic halide (the chlorine analysis was determined to be 4.7%).

EXAMPLE 1

Into a 4 liter high pressure autoclave, 1,147 grams of polyolefinic halide (produced as described) was transferred via a pressure bomb. Immediately following this, 692 grams of ethylene diamine was added to the autoclave via a second pressure bomb. The autoclave was sealed and pressurized to about 60 PSIG and the temperature increased to 170° C. with constant stirring. This temperature was maintained for about 5 hours. A portion of the material was transferred to a flask where the free amine was distilled. Aqueous sodium hydroxide was added to free the amine reacted with the amine.HCl salts. Following this, water and free amine were distilled. A portion of the mixture was transferred to a high pressure filter for separation of the solids.

Several attempts were made to filter the solids:
Attempt A: #1 Watman filter paper, no filter aid, 75 PSIG, unable to filter
Attempt B: #1 Watman filter paper, with filter aid #1, 75 PSIG, unable to filter
Attempt C: #1 Watman filter paper, with filter aid #2, 40 PSIG, able to filter 30 ml after ½ hour.

Analysis of filtered material showed: 2.3% nitrogen, 1300 ppm of ionic chloride.

Significance: The nitrogen analysis demonstrates that the process is effective at reacting polyolefinic halide with ethylene diamine; however, the solids produced during the reaction could not be easily filtered. The 1300 ppm of ionic chloride in the polyolefinic amine is unacceptable. This experiment demonstrates the reason most polyolefinic amine manufacturing relies upon a series of water/butanol wash steps to remove the finely dispersed solids.

EXAMPLE 2

In a flask, 99 grams of polyolefinic halide (produced as previously described) were reacted with 25 grams of dimethylaminopropylamine at a temperature of 125° C. for about 100 minutes with constant stirring; 15 grams of ethylene diamine was added to the polyolefinic halide dimethylaminopropylamine mixture. The flask temperature was increased to about 145° C. over a period of 200 minutes with stirring and reflux. The total reaction time was 300 minutes. Following the reaction, the reflux equipment was replaced with distillation equipment and the free amine removed as the temperature was increased to about 160° C. The flask was cooled to 70° C. and aqueous sodium hydroxide was added at a stoichiometric excess of 1.1 to 1.2 relative to the initial polyolefinic halide. The mixture was stirred as the temperature was increased to 160° C. as the water and free amine (amine freed from the amine.HCl salts) were distilled. The material in the flask was clear and bright, with a dark straw color, with a layer of solids at the bottom. A sample was decanted from the flask and analyzed for nitrogen and chlorine and found to contain 2.3% nitrogen and 90 ppm ionic chloride. A portion of the sample was filtered through #1 Watman filter paper without filter aid. A portion was centrifuged. The filtered and centrifuge samples contained the same concentration of ionic chloride and nitrogen.

Significance: The results demonstrate that the process described in this example effectively reacts polyolefinic halide with ethylene diamine and the solids can be easily filtered from the polyolefinic amine.

Additional analysis was conducted to verify that the sample described by Example 2 was free of dimers and trimers. Gel permeation chromatography (GPC) analysis was conducted. For reference, unreacted polyolefin and a commercial polyolefinic amine are presented. The number average molecular wt., $\overline{M}n$ was selected as the characteristic most descriptive for these samples.

| Sample | $\overline{M}n$ | % Difference |
| --- | --- | --- |
| A. Unreacted polyolefin | 1,097 | N.A. |
| B. Example 2 sample | 1,071 | −2.4 |
| C. Commercial sample | 1,952 | +77.9 |

Significance: The results demonstrate that the sample from Example 2 did not increase $\overline{M}n$, verifying that crosslinking producing dimers and trimers did not occur. The 2.4% difference between A and B is within experimental variability. The commercial sample C showed a 77.9% increase relative to the unreacted polyolefin.

Further analysis combining the GPC results with nitrogen analysis for the polyolefinic amines (B and C) demonstrates that sample B contains about 65% more reacted nitrogen than sample C. This difference is due to the reduced number of polyolefinic halide reaction sites resulting from the formation of dimers and trimers during the manufacturing of C.

EXAMPLE 3

In a flask, 95 grams of polyolefinic halide (produced as previously described) was reacted with 24 grams of dimethylamino propylamine (2.5 molar ratio of PIB-chloride to DMAPA) at a temperature of 125° C. for 100 minutes with stirring and reflux; 45 grams of tetraethylenepentamine was added to the polyolefinic halide dimethylaminopropylene mixture. The flask temperature was increased to about 145° C. over a period of 200 minutes with stirring and reflux. The total reaction time was 300 minutes. Following the reaction, the reflux equipment was replaced with distillation equipment and the free, dimethylamino-propylamine was removed. The contents of the flask were contacted with HCL to convert unreacted amine to amine HCL. The contents were transferred to a pressure funnel with #1 Watman filter paper and the amine.HCl crystals were separated from the polyolefinic amine. The amine.HCl crystals were transferred to a clean flask and aqueous NaOH was added at a stoichiometric excess to recover the amine. The water and dimethylamino-propylamine was distilled and the tetraethylenepentamine was filtered from the solids. Analysis of the polyolefinic amine after simple filtration through #1 Watman filter paper without filter aid and less than 5 PSIG pressure showed 3.1% nitrogen and about 100 ppm of ionic chloride.

One of the significant advantages of the process of the present invention is the manner in which it facilitates the recovery of unreacted amine. When PIB-Cl is reacted with EDA, excess EDA formed EDA.HCl crystals during the reaction which are too small to filter, and it is necessary to employ a series of water wash steps for product purification. The sequential reaction steps provided by the process of the present invention promote first the growth of large, easily filterable DMAPA.HCl crystals and then later formed EDA.HCl crystals which grow epitaxially upon those crystals already present, providing amine.HCl crystals which are much easier to filter and remove, thereby substantially simplifying product purification.

It is commonly accepted in the art that liquid hydrocarbon distillate fuel compositions containing polyamines such as those produced according to the present invention effectively counteract, nullify and/or inhibit fouling of vital parts of internal combustion engines.

The process of the present invention will carry out the objects set forth hereinabove. It is, therefore, to be understood that any variations evident fall within the scope of the claimed invention and thus, the selection of specific reactants as well as processing conditions can be determined without departing from the spirit of the invention herein disclosed and described. In particular, deposit control fuel additives according to the present invention are not necessarily limited to those having the amines exemplified herein or the mole ratios employed. Moreover, as noted hereinabove, other reaction temperatures can be substituted for those disclosed herein. Thus, the scope of the invention shall include all modifications and variations that may fall within the scope of the attached claims.

Having described the invention, the following is claimed:

1. A method of synthesizing polyolefinic amines or polyether amines, comprising the steps:

(a) forming a polymeric halide;

(b) reacting said polymeric halide with from about 0.01 to about 0.99 molar equivalent of a polyamine having only one reactive amine, for a period of from about 0.5 to about 15.0 hours at a temperature of from about 75° F. to about 410° F. at a pressure of from about 0 to about 6 atmospheres;

(c) adding to said reaction mass at least one additional polyamine having at least two primary amine moieties, in an amount equal to from 0.01 to about 10 times the molar quantity of polyolefinic halide employed to form the first reaction mass and reacting said second reaction mass for a period of from about 1 to about 15 hours at a temperature of from about 75° F. to about 410° F. at a pressure of from about 0 to about 6 atmospheres;

(d) distilling off any unreacted polyamine at a distillation temperature below about 400° F; and, (e) treating said second reaction mass to recover polyolefinic amine products.

2. The method according to claim 1 wherein said first reacting step is carried out for from about 0.5 to about 3 hours at a temperature of from about 175° F. to about 360° F. at a pressure of from about 1 to about 6 atmospheres and said second reacting step is carried out in the presence of a molar excess of amine in the range of from 3 to about 8 times the molar quantity of polymeric halide or polyether halide employed to form the first reaction mass and for from about 2 to about 5 hours at a temperature of from about 175° F. to about 360° F. at a pressure of from about 0 to about 6 atmospheres.

3. The method of claim 1 wherein any unreacted amine remaining in said second reaction mass after said distillation step is reacted with HCl to convert the unreacted amine to amine.HCl.

4. The process according to claim 2 wherein said polyolefinic halide is PIB.Cl, said first reacting step employs DMAPA and said second reacting step employs a mixture of DMAPA and EDA in a molar ratio of from about 1:10 to about 10:1.

5. The method according to claim 1 wherein an HCl acceptor is added following the formation of the polymeric halide.

6. The process according to claim 1 wherein said polymeric halide is first reacted with an amine having one reactive nitrogen and then reacted with a member selected from the group consisting of amines having at least two primary nitrogens, and mixtures of amines having at least two primary nitrogens and amines having one primary nitrogen.

7. The process according to claim 2 wherein an HCl acceptor is added following the formation of the polymeric halide.

8. A method for controlling the ratio of reactive polyolefinic halide sites relative to the reactive polyamine reactive sites, comprising the steps of:

(a) forming a polymeric halide;

(b) reacting said polymeric halide with from 0.01 to 0.99 molar equivalent of a polyamine having only one reactive amine for a period of time from about 0.5 to about 15.0 hours at a temperature of from about 75° F. to about 410° F. at a pressure of from about 0 to about 6 atmospheres;

(c) adding to said reaction mass at least one additional polyamine having at least two primary amine moieties, in an amount equal to from 0.01 to about 10 times the molar quantity of polyolefinic halide employed to form the first reaction mass and reacting said second reaction mass for a period of time from about 1 to about 15 hours at a temperature of from about 75° F. to about 410° F. at a pressure of from about 0 to about 6 atmospheres;

(d) distilling off any unreacted polyamine at a distillation temperature below about 400° F; and, (e) treating said second reaction mass to recover polyolefinic amine products.

9. A process for controlling the size and morphology of solid crystals produced during the manufacturing of polyolefinic amines and polyetheramines, the steps which comprise:

(a) forming a polymeric halide;

(b) reacting said polymeric halide with from 0.01 to 0.99 molar equivalent of a polyamine having only one reactive amine, for a period of from about 0.5 to about 15.0 hours at a temperature of from about 75° F. to about 410° F. at a pressure of from about 0 to about 6 atmospheres;

(c) adding to said reaction mass at least one additional polyamine having at least two primary amine moieties, in an amount equal to from 0.01 to about 10 times the molar quantity of polyolefinic halide employed to form the first reaction mass and reacting said second reaction mass for a period of from about 1 to about 15 hours at a temperature of from about 75° F. to about 410° F. at a pressure of from about 0 to about 6 atmospheres;

(d) distilling off any unreacted polyamine at a distillation temperature below about 400° F.; and, (e) treating said second reaction mass to recover polyolefinic amine products.

10. A process for recovering high boiling point amines from the manufacturing of polyolefinic amines by reacting the free amines to form solid amine salts, the steps which comprise:

(a) forming a polymeric halide;

(b) reacting said polymeric halide with from 0.01 to 0.99 molar equivalent of a polyamine having only one reactive amine, for a period of from about 0.5 to about 15.0 hours at a temperature of from about 75° F. to about 410° F. at a pressure of from about 0 to about 6 atmospheres;

(c) adding to said reaction mass at least one additional polyamine having at least two primary amine moieties, in an amount equal to from 0.01 to about 10 times the molar quantity of polyolefinic halide employed to form the first reaction mass and reacting said second reaction mass for a period of from about 1 to about 15 hours at a temperature of from about 75° F. to about 410° F. at a pressure of from about 0 to about 6 atmospheres;

(d) distilling off any unreacted polyamine at a distillation temperature below about 400° F.;

(e) contacting the contents of the flask with HCl to convert unreacted amine to amine.HCl; and, (f) filtering said reaction mass to recover said polyolefinic high boiling point amines as filtrate and said any other amines as amine chloride crystals.

11. A method of synthesizing polyolefinic amines or polyester amines, comprising the steps of:

(a) forming a polymeric halide;

(b) reacting said polymeric halide with from about 0.01 to about 0.99 molar equivalent of a polyamine, which polyamine comprises a mixture of at least one polyamine having only one reactive amine moiety and at least one polyamine having at least two primary amine moieties in an amount equal to from about 1.0 to about ten times the molar quantity of polyolefinic halide or polyether halide added together with the polymeric halide, for a period of time from about 0.5 to about 15.0 hours at a temperature from about 75° F. to about 410° F. at a pressure of from about 0 to about 6 atmospheres;

(c) distilling off any unreactive polyamine at a distillation temperature below about 400° F.; and, (d) treating said reaction mass to recover polyolefinic amine products.

12. The process of claim 11 wherein an HCl acceptor is added following the formation of the polymeric halide.

13. The method of claim 11 wherein any unreacted amine remaining in said reaction mass is reacted with HCl to convert the unreacted amine to amine HCl.

* * * * *